US009149938B1

(12) United States Patent
Summer et al.

(10) Patent No.: US 9,149,938 B1
(45) Date of Patent: Oct. 6, 2015

(54) ROBOTIC EXOSKELETON WITH ADAPTIVE VISCOUS USER COUPLING

(71) Applicant: HARRIS CORPORATION, Melbourne, FL (US)

(72) Inventors: Matthew D. Summer, Melbourne, FL (US); Paul M. Bosscher, West Melbourne, FL (US)

(73) Assignee: Harris Corporation, Melbourne, FL (US)

( * ) Notice: Subject to any disclaimer, the term of this patent is extended or adjusted under 35 U.S.C. 154(b) by 6 days.

(21) Appl. No.: 14/302,528

(22) Filed: Jun. 12, 2014

Related U.S. Application Data

(60) Provisional application No. 61/978,545, filed on Apr. 11, 2014.

(51) Int. Cl.
| G05B 19/04 | (2006.01) |
| G05B 19/18 | (2006.01) |
| B25J 19/00 | (2006.01) |
| B25J 9/00 | (2006.01) |
| B25J 9/16 | (2006.01) |

(52) U.S. Cl.
CPC ............ *B25J 19/0091* (2013.01); *B25J 9/0006* (2013.01); *B25J 9/1674* (2013.01); *Y10S 901/49* (2013.01)

(58) Field of Classification Search
USPC .................. 700/253, 245, 250; 600/595, 587; 482/69; 601/5; 623/24, 26, 27, 40, 53, 623/31
See application file for complete search history.

(56) References Cited

U.S. PATENT DOCUMENTS

| 8,419,804 | B2* | 4/2013 | Herr et al. ....................... 623/24 |
| 8,702,811 | B2* | 4/2014 | Ragnarsdottir et al. ......... 623/47 |
| 8,986,397 | B2* | 3/2015 | Bedard et al. ................... 623/47 |
| 9,066,817 | B2* | 6/2015 | Gilbert et al. ......................... 1/1 |
| 2006/0079817 | A1* | 4/2006 | Dewald et al. ................... 601/5 |
| 2007/0123997 | A1* | 5/2007 | Herr et al. ....................... 623/27 |
| 2009/0255531 | A1* | 10/2009 | Johnson et al. .............. 128/99.1 |
| 2011/0266323 | A1* | 11/2011 | Kazerooni et al. ............. 224/575 |
| 2012/0156661 | A1* | 6/2012 | Smith et al. ................... 434/219 |
| 2012/0259431 | A1* | 10/2012 | Han et al. ........................ 623/24 |
| 2013/0102935 | A1* | 4/2013 | Kazerooni et al. .............. 601/35 |

* cited by examiner

*Primary Examiner* — Ronnie Mancho
(74) *Attorney, Agent, or Firm* — Robert J. Sacco; Carol E. Thorstad Forsyth; Fox Rothschild LLP (57) ABSTRACT

A system for preventing discomfort to a user of a robotic exoskeleton (200) determines the existence of an exoskeleton operating condition which has the potential to cause at least one of a discomfort or an injury to a user (204) when the exoskeleton is being worn by the user. Responsive to the determining, an exoskeleton control system (224) selectively controls at least one viscous coupling (208, 210) disposed at an interface location (201, 203) of the exoskeleton where a physical interaction occurs between a portion of the user and a portion of the exoskeleton when the exoskeleton is in use. The control system selectively varies a viscosity of a fluid (216) comprising the viscous coupling to control the stiffness of the interface.

18 Claims, 7 Drawing Sheets

ROBOTIC EXOSKELETON WITH ADAPTIVE VISCOUS USER COUPLING

CROSS REFERENCE TO RELATED APPLICATIONS

This application claims the benefit of U.S. Provisional Patent Application No. 61/978,545, filed Apr. 11, 2014, the entirety which is incorporated herein by reference.

BACKGROUND OF THE INVENTION

1. Statement of Technical Field

The inventive arrangements relate to robotic exoskeletons and more particularly to robotic exoskeletons having advanced control systems and interface components that facilitate user safety.

2. Description of the Related Art

A robotic exoskeleton is a machine that is worn by a human user. Such machines typically comprise a structural frame formed of a plurality of rigid structural members. The structural members are usually connected to each other at a plurality of locations where joints or articulated members allow movement of the structural members in a manner that corresponds to movement in accordance with the human anatomy. When the exoskeleton is worn by a user, the location of many of the robotic joints will often correspond to the location of joints in the human anatomy. Motive elements, which are sometimes called actuators, are commonly used to facilitate movement of the rigid structural members that comprise the exoskeleton. These motive elements or actuators commonly include hydraulic actuators, pneumatic actuators and/or electric motors. Various exoskeleton designs for humans have been proposed for the full body, lower body only, and upper body only.

An exoskeleton includes a power source to operate the motive elements or actuators. The power source for such devices can be an on-board system (e.g. batteries, or fuel driven power generator carried on the exoskeleton). Alternatively, some exoskeleton designs have a wire or cable tether which supplies power (e.g. electric or hydraulic power) from a source which is otherwise physically independent of the exoskeleton. An on-board control system is provided in many exoskeletons to allow a user to control certain operations of the exoskeleton. Due to the close interaction of the exoskeleton with the human operator, such a control system for the exoskeleton must be carefully designed to facilitate ease of use and operator safety.

Robotic exoskeletons as described herein can provide users with advantages of increased strength, endurance and mobility. The motive elements used to produce movement of the structural members forming the exoskeleton can in many designs exert forces that far exceed the strength and/or endurance of a human. Exoskeletons can also potentially increase user safety and help control certain desired motions. As such, robotic exoskeletons are of increasing interest for use in a wide variety of applications. For example, robotic exoskeletons have potential for use in the fields of healthcare, physical rehabilitation, and public service (police, first responders). Exoskeletons also show promise for use in areas such as human augmentation.

SUMMARY OF THE INVENTION

The invention concerns an exoskeleton system comprised of a plurality of structural members, one or more robotic joints at which the plurality of structural members are movably attached, and a plurality of actuators connected to the structural members which are capable of providing a motive force for moving the structural members in relation to the robotic joints. The structural members and robotic joints are arranged to facilitate movement of the exoskeleton in conformance with at least a portion of a human anatomy when the exoskeleton is worn by a user. A control system is provided that is responsive to at least one input signal from the exoskeleton to generate actuator control signals which control the plurality of actuators. The exoskeleton includes at least one viscous coupling disposed at an interface location of the exoskeleton where a physical interaction occurs between a portion of the user and a portion of the exoskeleton when the exoskeleton is in use. The viscous coupling is comprised of a fluid having a viscosity that is selectively variable responsive to viscosity control signals from the control system.

The invention also concerns a method for preventing discomfort to a user of a robotic exoskeleton. The method involves determining the existence of an exoskeleton operating condition which has the potential to cause at least one of a discomfort or an injury to a user when the exoskeleton is being worn by the user. Responsive to the determining, the exoskeleton control system selectively controls at least one viscous coupling disposed at an interface location of the exoskeleton where a physical interaction occurs between a portion of the user and a portion of the exoskeleton when the exoskeleton is in use. The control system selectively varies a viscosity of a fluid comprising the viscous coupling to control the stiffness of the interface.

BRIEF DESCRIPTION OF THE DRAWINGS

Embodiments will be described with reference to the following drawing figures, in which like numerals represent like items throughout the figures, and in which.

DETAILED DESCRIPTION

The invention is described with reference to the attached figures. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operation are not shown in detail to avoid obscuring the invention. The invention is not limited by the illustrated ordering of acts or events, as some acts may occur in different orders and/or concurrently with other acts or events. Furthermore, not all illustrated acts or events are required to implement a methodology in accordance with the invention.

Due to the close interaction of the exoskeleton with the human operator, a user/machine interface for the exoskeleton must be carefully designed to facilitate optimal operator comfort, control and safety. A common problem which occurs with a robotic exoskeleton involves the amount of force transmitted to the user during robotic exoskeleton operation. For many applications, the ability of a user to feel the interaction with the environment is critical (e.g. while using a powered hand tool). If the human operator is completely isolated from forces exerted upon the exoskeleton, then tactile feedback for the user is eliminated. In such a scenario, the exoskeleton tends to inhibit user interaction and sensing of the working environment. Still, it is not desirable to have the operator experience contact forces applied to the exoskeleton under all conditions. For example, large contact forces could fatigue or injure the operator. The inventive arrangements address the foregoing concerns by using a viscous coupling to adaptively modify a physical interface between a user and an exoskeleton. The viscosity of the interface is selectively controlled (e.g. by a robotic exoskeleton controller) to provide optimal operator comfort, control and/or safety. The control system is advantageously arranged to perform these interface control functions based on an evaluation of certain exoskeleton operating conditions and/or in response to specific user commands.

Figure 1:
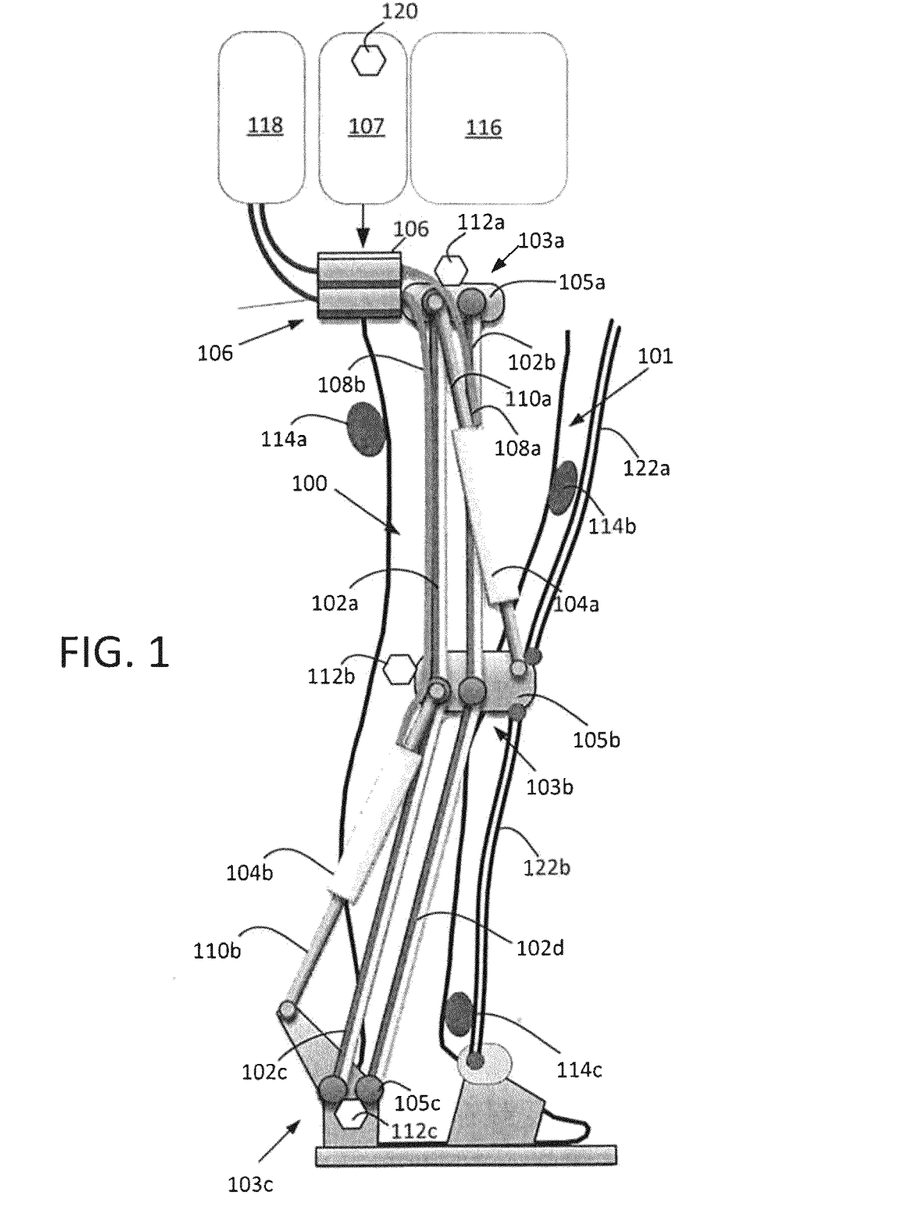
FIG. 1 is a drawing that is useful for understanding the various elements of an exoskeleton.

Referring now to FIG. 1 there is shown a portion of an exemplary exoskeleton 100 that is useful for understanding an exoskeleton viscous user interface coupling. For convenience, the portion of the exoskeleton shown in FIG. 1 is from the waist down. However, it should be understood that the inventive arrangements described herein can also apply to other selected portions of an exoskeleton, such as an upper portion of an exoskeleton worn on an upper body part of user. The exoskeleton 100 is formed of a plurality of rigid structural members 102a, 102b, 102c, and 102d which are connected to each other at a plurality of joint locations 103a, 103b, 103c where one or more robot joints 105a, 105b, 105c are provided.

The joint locations and the robot joints are arranged to facilitate movement of the rigid structural members in a manner that at least partially corresponds to movement in accordance with the anatomy of a human user when the exoskeleton is being worn by such user. For example, when a user 101 who wears the exoskeleton 100 bends his knee, the structural members 102a, 102b, 102c, and 102d will pivot at robot joint 105b to facilitate such user movement. Other portions of the exoskeleton can be similarly designed to facilitate movement with the user. Consequently, the rigid structural members and the plurality of robot joints comprising an exoskeleton can be fitted to and move with at least one portion of a user 101. For example, the body portions can include all or part of an upper body portion which extends over parts of the human body above the waist, a lower body portion which extends over parts of the human body below the waist, and a full body portion comprising the upper and lower body parts.

The exoskeleton 100 also includes one or more motion actuators (e.g. motion actuators 104a, 104b). One or more of the motion actuators can be comprised of pneumatic actuators such as pneumatically operated pistons as shown. Still, the invention is not limited in this regard and other types of motion actuators may also be used. For example, one or more of the motion actuators can optionally be comprised of hydraulic actuators, and/or electric motors.

In operation, the motion actuators exert motive forces directly or indirectly upon the structural members to facilitate movement and other operations associated with the exoskeleton. For example, in the case of the pneumatic type actuators shown in FIG. 1, pressurized gas or air is communicated to an internal cylinder (not shown) associated with the actuator. The operation of pneumatic actuators is well known in the art and therefore will not be described here in detail. However, it will be appreciated that the pressurized air in the cylinder can move an internal piston (not shown) that is coupled to a rod 100a, 110b. The rod is connected to the exoskeleton structure at a suitable location, such as robot joint 105a, 105c. The flow of pressurized air or gas to the cylinder of the pneumatic actuator can be communicated by any suitable means such as pneumatic air lines 108a, 108b. One or more valves 106 can control a flow of air to the pneumatic actuators.

An outer cover for the exoskeleton can be comprised of one or more cover portions (e.g. cover portions 122a, 122b). The cover portions will partly or completely enclose portions of the exoskeleton and/or the person wearing such exoskeleton. The outer cover can be attached to the rigid structural members (e.g. rigid structural members 102a, 102b, 102c, and 102d). Alternatively, or in addition the outer cover can be attached to one or more of robot joints (e.g. robot joints 105a, 105b, 105c). The cover portions (e.g. cover portions 122a, 122b) of the exoskeleton can complement the function of the structural members (e.g. rigid structural members 102a, 102b, 102c, and 102d) to provide some of the necessary structural rigidity for the exoskeleton. In some instances, the functionality of the rigid structural members comprising the exoskeleton can be combined with the functionality of the cover portions. In such embodiments, one or more of the cover portions can serve as both a cover and as part of an integrated structural framework of the exoskeleton.

In FIG. 1, cover portions 122a, 122b are shown as extending over a front portion of an exoskeleton 100 to partially enclose a user 101. However, it will be appreciated that the cover portions can extend over greater or lesser parts of the exoskeleton. In the inventive arrangements, the cover portions are rigid or semi-rigid structural members which are advantageously provided to protect the operator and/or the internal components of the exoskeleton. The cover portions are also useful to facilitate certain other user-machine interface functions as described below in relation to FIGS. 2 and 3.

A control system 107 can facilitate operator control of the exoskeleton actuators to carry out exoskeleton movements and operations. The control system can also control certain functions pertaining to a physical interface between the exoskeleton and user. These interface control functions can be advantageous for ensuring user safety, convenience, and comfort in relation to exoskeleton operation. A control system 107 used with the inventive arrangements can comprise any suitable combination of hardware and software to carry out the control functions described herein. As such, the control system can comprise a computer processor programmed with a set of instructions, a programmable micro-controller or any other type of controller. The control system is arranged to communicate with one or more controlled elements for carrying out the interface control functions described herein. For example, in the exemplary exoskeleton system 100 shown in FIG. 1, the controlled elements can include one or more viscous interfaces provided between a human operator and one or more rigid parts of the exoskeleton.

The exoskeleton will include a plurality of sensors which communicate sensor data to the control system 107. For example, sensors 112a, 112b, 112c can be provided at one or more robot joints to provide sensor data regarding a position, a displacement and/or an acceleration of one or more structural members 102a, 102b, 102c, 102d relative to other parts of the exoskeleton. Additional sensors 114a, 114b, 114c can be provided to sense movements or forces exerted by the operator or user 101 upon the exoskeleton 100. Output sensor data from these additional sensors 114a, 114b, 114c can be interpreted by control system 107 as control signals which can cause certain operations of motion actuators 104a, 104b. For example, the control system can respond to inputs from such sensors to activate certain motion actuators for effecting movement of the exoskeleton. Finally, one or more sensors 120 can be provided to measure overall acceleration and or velocity of an exoskeleton 100 as a whole relative to an external frame of reference (e.g. relative to the earth). Connections between the various sensors and the control system are omitted in FIG. 1 to avoid obscuring the invention. However, it will be appreciated by those skilled in the art that suitable wired or wireless connections are provided to communicate sensor data from each sensor to the control system.

A suitable power source 116 is provided for powering operations of the exoskeleton. The power source can provide a source of electrical power for electronic components, such as the control system. The power source can comprise a battery, a fuel-based power generator or a tethered connection to an external power source. For exoskeletons that use pneumatic or hydraulic actuators, the exoskeleton can also include a source 118 of pressurized air or hydraulic fluid. The power source 116 and the source 118 of pressurized air can be carried on-board the exoskeleton or can be provided from a remote base unit by means of a tether arrangement.

In an exoskeleton 100 there are one or more locations where a human operator who is wearing the exoskeleton will physically interact with the exoskeleton. For example, these physical points of interaction can be at locations corresponding to sensors which sense movements or forces exerted by the user 101 upon the exoskeleton 100. An exemplary part of an exoskeleton at which a human/machine interface is provided is often at a user's hands. Exoskeleton structures that correspond to a user's hands are particularly important areas of human/exoskeleton interface because the operational requirements often demand a high level of dexterity and user tactile sensitivity. These requirements arise due to the common necessity to perform tasks in a very precise and controlled manner. But these exoskeleton hand interface requirements can conflict with concerns that arise in other operational scenarios which involve shock loads being imparted to the exoskeleton. Operator safety and comfort can, in some scenarios, suggest the need for cushioning or other kinds of energy absorbing structures at the interface between the operator and the exoskeleton.

Figure 2A:
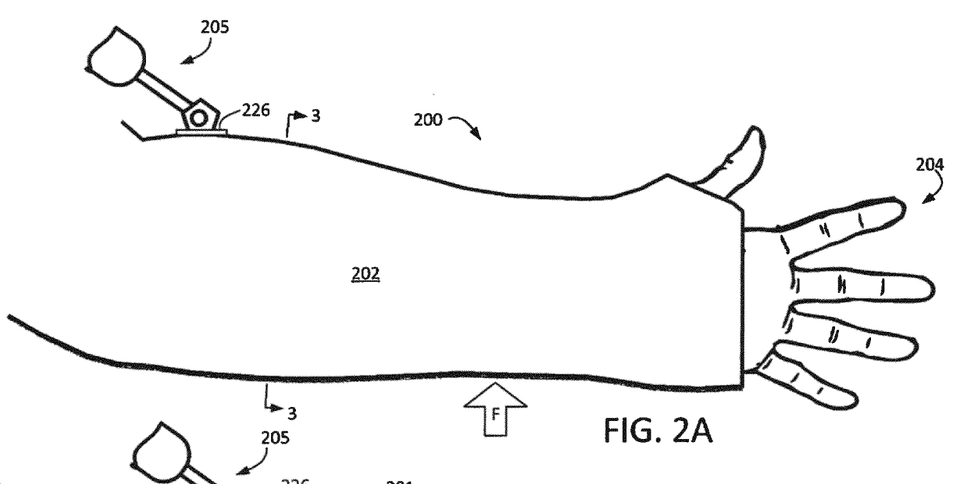
FIG. 2A is a drawing that is useful for understanding how an adaptive viscous user coupling can be provided in an exoskeleton.
Figure 2B:
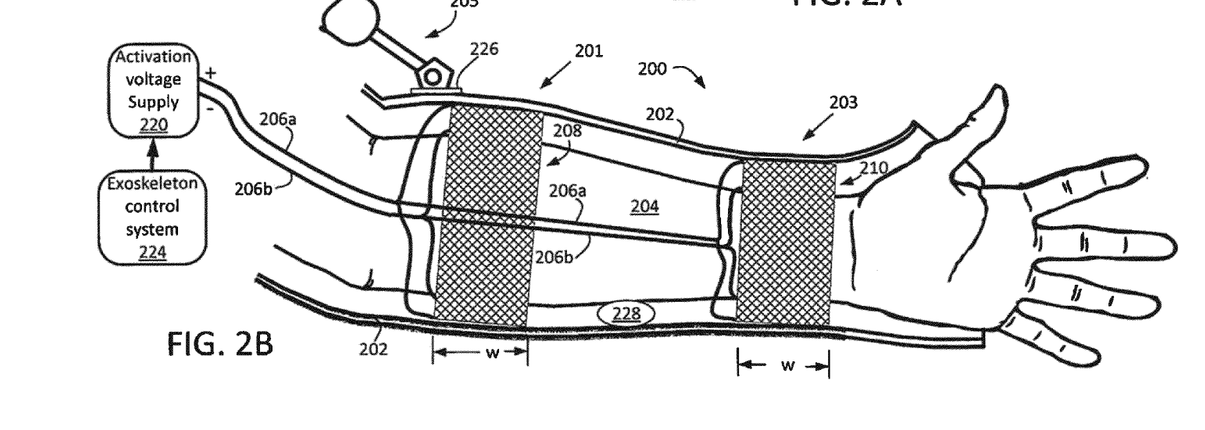
FIG. 2B shows the exoskeleton in FIG. 2A, with a portion of the exoskeleton cut away to reveal an internal viscous coupling arrangement.
Figure 2C:
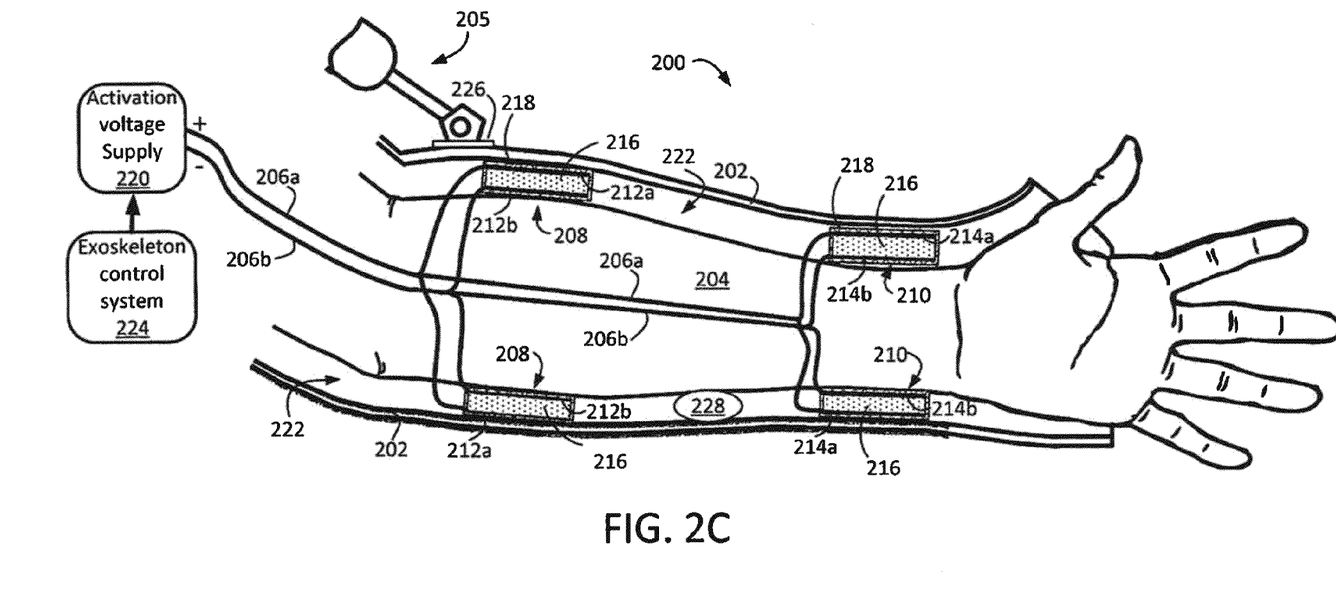
FIG. 2C shows the exoskeleton in FIG. 2A with a portion of the exoskeleton cut-away to reveal the internal viscous coupling arrangement, and with the viscous coupling shown in cross-section to reveal its internal features.

Referring now to FIGS. 2A-2C, there is shown a portion of an exoskeleton 200 which extends along the length of an arm of a user. Exoskeleton 200 can be a full body exoskeleton which extends above and below the waist of an operator when worn. Alternatively, the exoskeleton 200 can extend over lesser portions of a user's anatomy. The exoskeleton 200 includes a cover portion 202. For convenience, it shall be assumed for purposes of this embodiment that the cover portion 202 also serves as a structural member comprising the exoskeleton. The exoskeleton 200 can include one or more additional components such as actuators (e.g. actuator 205), robot joints, and/or sensors, as described above with respect to FIG. 1. To avoid obscuring the invention, some of these components are not shown in FIGS. 2A-2C.

The exoskeleton 200 includes one or more viscous interfaces between a human operator 204 and an exoskeleton cover portion 202. The viscous interfaces are provided by means of one or more fluid-filled pads/sleeves 208, 210 which serve as viscous coupling members. These pads or sleeves provide a dynamic physical interface between the user or operator 204 and portions of the exoskeleton 200 which surround such operator. Accordingly, the pads or sleeves can be disposed at a plurality of contact zones 201, 203 where the operator is physically engaged with or interfaced with an exoskeleton. In FIGS. 2A-2C, the fluid filled sleeves 208, 210 are arranged to contact portions of an operator's forearm; however, it should be understood that the inventive arrangements can apply to any portion of the exoskeleton where an operator comes in contact with a rigid structural part of the exoskeleton. Accordingly, the forearm arrangement in FIGS. 2A-2C is shown merely for purposes of illustration.

Figure 3:
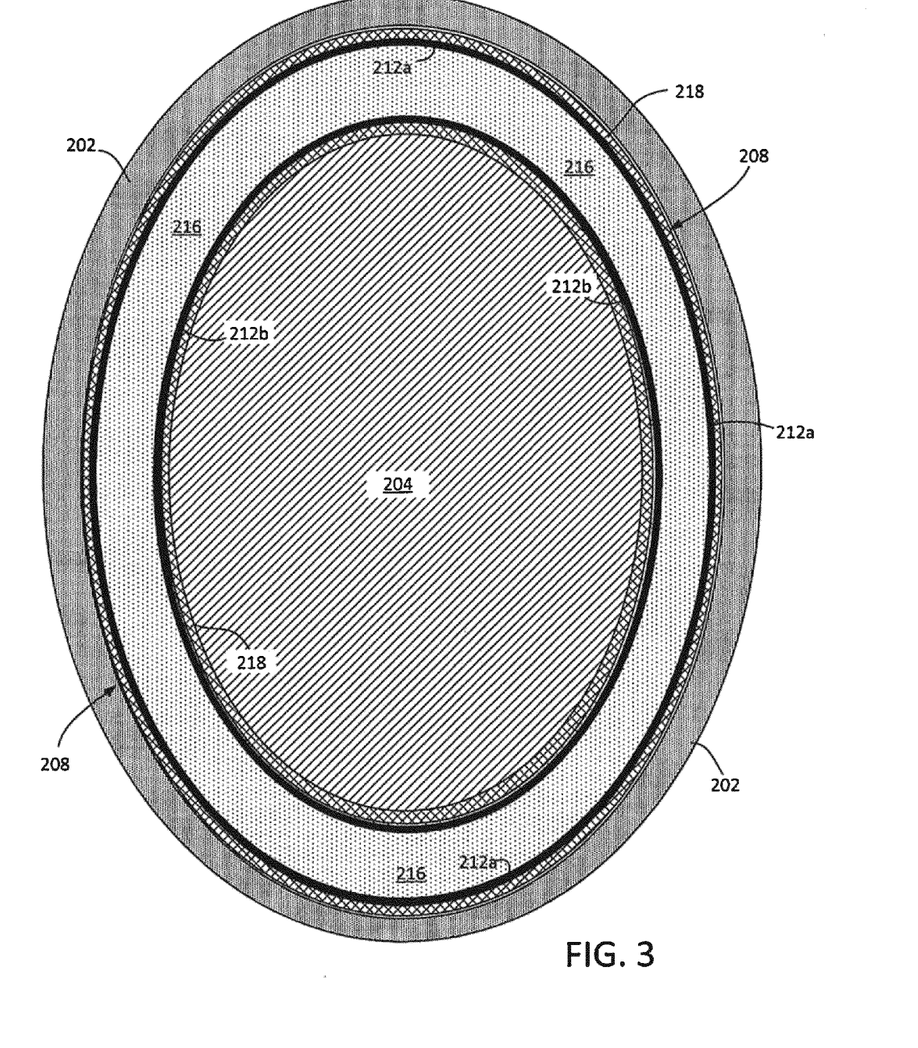
FIG. 3 is a cross-sectional view of FIG. 2A taken along line 3-3.

As shown in FIGS. 2C and 3 sleeves 208, 210 are comprised of a flexible fluid containment layer 218 which defines an internal cavity filled with a viscous fluid 216. The viscous fluid 216 fills the internal cavity defined by each sleeve 208, 210 and each sleeve is advantageously sized so that it completely fills an air gap 222 between the operator's forearm and the cover portion 202 in the area defined by the respective contact zones 201, 203. The fluid containment layer can be comprised of any type of flexible membrane that is capable of containing a viscous fluid 216. In some embodiments, the containment layer 218 can be comprised of multiple material layers. For example, the fluid containment layer can be comprised of an inner layer of flexible polymer or rubber-like material that is suitable for containing the fluid 216, and an outer layer of a textile material that is chosen for operator comfort and/or to protect the inner layer from abrasion. In the embodiment shown, the sleeve is shaped as a toroid so that it extends fully around the forearm of the user at a contact zone.

In the exemplary embodiment shown in FIGS. 2A-2C, the user's forearm fits snugly within the inner portion of the toroidal shaped sleeves and the outer portion of each toroidal sleeve is snugly disposed against the exoskeleton cover portion 202. Of course, the embodiment shown is merely one possible example of how the viscous coupling could be arranged and other embodiments are also possible. For example in place of a toroidal shaped sleeve, a pad could be used instead. The pad may extend only partially around the forearm instead of completely around the forearm as shown. Also, the pad or sleeve could be located at other locations to provide a dynamic interface between other portions of the operator's anatomy and the exoskeleton. For example, the viscous interface could be disposed between portions of the user and the exoskeleton at the user's hand, upper arm, upper body, legs or feet.

According to one aspect of the invention, the fluid 216 contained within each of the sleeves 208, 210 is advantageously one that has a rapidly adjustable viscosity so that the rigidity or resiliency of the sleeves can be dynamically controlled. For example, fluids for which the viscosity can be controlled by an applied magnetic or electric field are ideal for this purpose. Accordingly, exemplary viscous fluids useful for this purpose include electrorheological (ER) fluid and magnetorehological (MR) fluid. The apparent viscosity of an ER fluid can be rapidly changed in a reversible manner in response to an applied electric field. For example, the apparent viscosity of an ER fluid can change by a factor of up to 100,000 in response to an electric field. This transition can occur very quickly (on the order of milliseconds). Magnetorheological (MR) fluid functions in a similar way, but in response to a magnetic field rather than an electric field. Both MR and ER fluids are well known in the art and therefore will not be described herein detail. However, it should be appreciated that one or more exciter elements can be used to selectively apply or vary an intensity of an applied electric or magnetic field.

According to one aspect of the invention, each sleeve 208, 210 will include one or more exciter elements 212a, 212b, 214a, 214b. The exciter elements are advantageously configured to stimulate the viscous fluid in such a way as to effect a rapid change in the viscosity of the viscous fluid 216 as described herein. The exciter elements are shown to be contained internal to the sleeves 208, 210 but the invention is not limited in this respect. The design of the exciter element and the type of stimulus will depend on the particular type of fluid being used. For example, if fluid 216 is an ER type fluid then exciter elements 212a, 212b, 214a, 214b can be comprised of flexible conductive plates. The exciter elements are preferably arranged so that substantially all of the fluid contained within each sleeve is exposed to the applied electric filed. For example, the exciter elements can have a width that is approximately equal to a width w of each sleeve, and can extend along an inner and outer circumference of the toroidal sleeve as shown in FIGS. 2C and 3. When arranged in this way, the two flexible conductive plates will form an electric field that extends across the width w of the sleeve, and is substantially uniform in intensity around the circumference of the sleeve. A voltage differential is established as between the exciter elements 212a, 212b and 214a, 214b so that an electric field is formed in the space between the two exciter elements. For example, the voltage differential can be established by an activation voltage supply 220. The voltage output of the activation voltage supply is coupled to the exciter elements by suitable means such as conductive wires 206a, 206b. The viscosity of the ER fluid can then be controlled by varying the DC voltage output of activation voltage supply.

In an alternative embodiment (not shown), one or both of the exciter elements can comprise a conductive wire coil to form an electromagnet which establishes a magnetic field when a DC voltage is applied to the coil. The arrangement of the exciter coils in such an embodiment is preferably such that an evenly distributed magnetic field of uniform intensity is formed in the space within the sleeve 208, 210 where the fluid 216 is contained. In this embodiment, the viscosity of the fluid (and hence the resiliency or stiffness of each sleeve) would be controlled by varying the intensity of the magnetic field. More particularly, the intensity of the magnetic field in such a scenario can be controlled by in accordance with current flowing through the wire coils. Of course, other types of exciter elements would be used to accommodate different types of fluids 216 that change viscosity in response to other types of stimuli. In this regard it should be appreciated that the fluid 216 can be any type of fluid now known or known in the future, wherein viscosity of such fluid can be rapidly controlled in response to an applied stimulus.

With the foregoing arrangement, viscosity of the fluid in a sleeve 208, 210 can be varied or changed very rapidly (on the order of milliseconds). For example, the viscosity can be changed or varied in accordance with the type of task a user is engaged in with an exoskeleton and/or in response to the magnitude of contact forces experienced or anticipated by the exoskeleton. According to one aspect of the invention, the fluid 216 can be controlled to provide a sleeve 208, 210 with high viscosity/stiffness under conditions of low load/low impact contact forces, and can be controlled to provide a sleeve with low viscosity/stiffness for high load/high impact forces.

A control system 224 facilitates operator control of the exoskeleton and control of fluid viscosity. A control system used with the inventive arrangements can comprise any suitable combination of hardware and software to carry out the control functions described herein. As such, the control system can comprise a computer processor programmed with a set of instructions, a programmable micro-controller or any other type of controller. The control system 224 can be arranged to communicate with the activation voltage supply for carrying out the fluid viscosity control described above.

One or more sensor elements (e.g. sensor 226, 228) are provided to sense certain conditions that are useful for determining a desired fluid viscosity or stiffness. These sensors are provided at suitable locations on or in the exoskeleton to determine a magnitude of a force applied to a particular portion of the exoskeleton 202. Force sensors can be used for this purpose to measure existing forces actually applied to various structural elements and at movable joints of the exoskeleton. However, other types of sensors can also potentially be used to facilitate control of the fluid. For example acceleration or velocity sensors can potentially be used to allow a control system to anticipate when substantial large forces are likely to occur. Consider a scenario in which an operator is swinging his arm to deliver a hammer-like strike to a surface. A sensed rapid acceleration of an upper body or arm portion of the exoskeleton (e.g. a motion consistent with swinging a hammer) would suggest that the viscosity of a viscous interface surrounding the operator's forearm should be reduced in anticipation of large impact forces. In this regard, the control system could be programmed to recognize certain exoskeleton movement patterns which terminate in large impact forces, and can adjust the fluid viscosity in anticipation of an expected impact force. Alternatively, if the control system senses that the operator is engaging in an activity involving highly controlled precise movements with minimal levels of measured force and/or acceleration, then it can be preferable to increase a viscosity of a viscous interface to facilitate fine motor control and tactile feedback to the operator.

Figure 4:
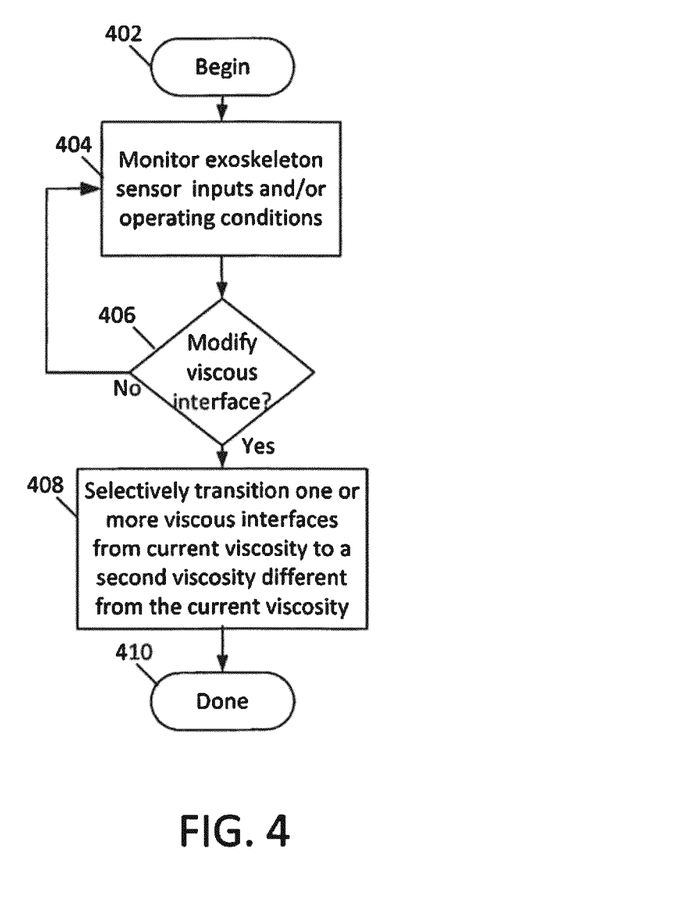
FIG. 4 is a flowchart that is useful for understanding a method of controlling an exoskeleton.

The foregoing concept is illustrated in FIG. 4 which shows a method for operating an exoskeleton using a viscous user interface. The process begins at 402 and continues at 404 where the control system monitors sensor inputs and other exoskeleton operating conditions. At 406, a determination is made as to whether the sensor inputs and/or operating conditions of the exoskeleton warrant a change in one or more viscous interfaces as described herein. If not (406: No) then the control system continues its monitoring operations; however, if the control system determines that a modification of one or more viscous interfaces is desirable, then the process continues on to step 408. At 408 the control system selectively transitions one or more viscous interfaces from a current viscosity to a second viscosity different from the current viscosity. Notably, it can be desirable in certain scenarios for different viscous interfaces to have different viscosities. In such scenarios, the control system can selectively control each of the viscous interfaces to have a particular desired viscosity.

Figure 5:
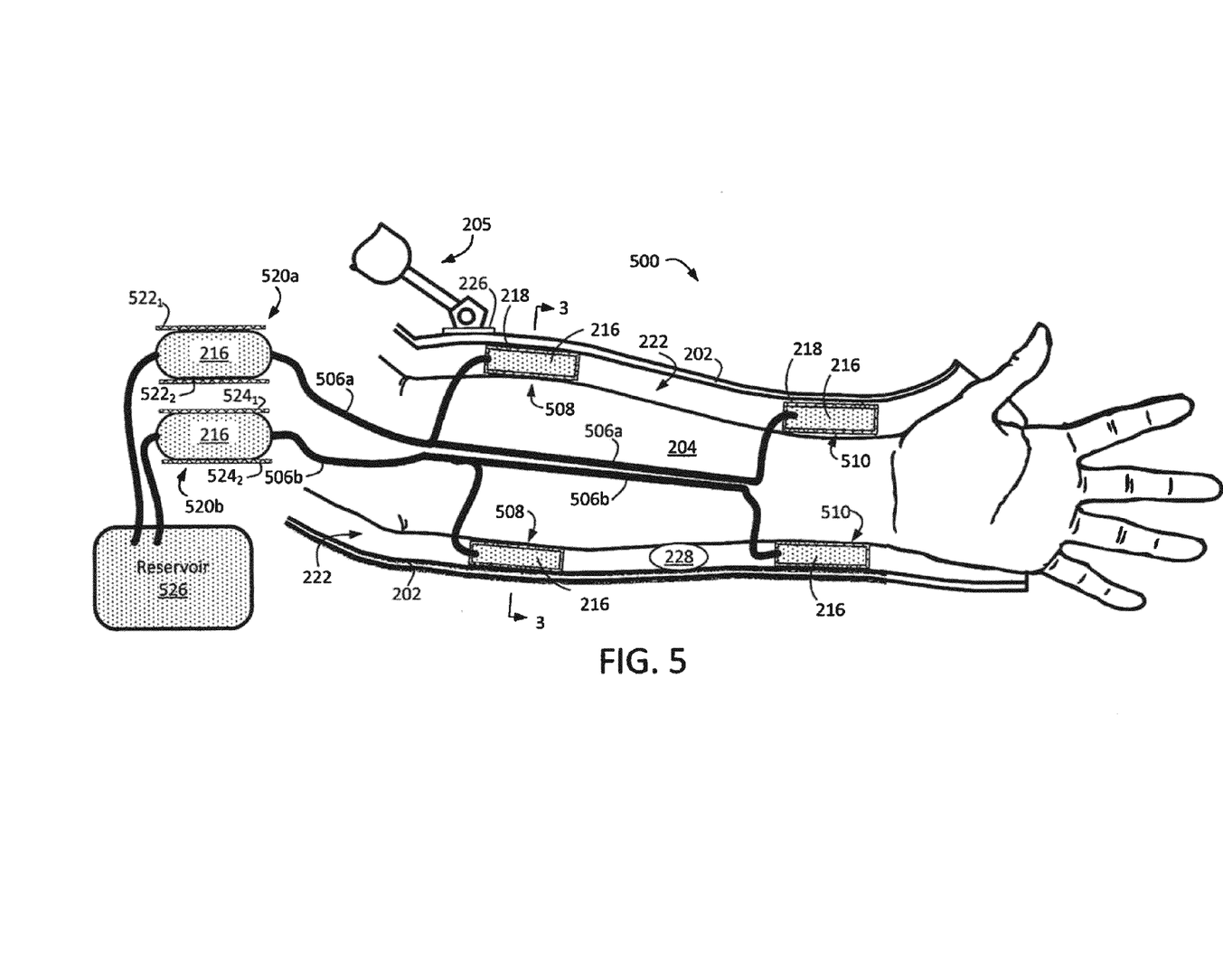
FIG. 5 is a cross-sectional view of a portion of an exoskeleton that is useful for understanding a first alternative embodiment of the invention.

Referring now to FIG. 5, there is shown an alternative embodiment of the inventive arrangements in which one or more viscous couplings are provided between a human operator 204 and an exoskeleton 500. The exoskeleton 500 is similar to the exoskeleton 200 except a somewhat different approach is used for controlling a stiffness of the viscous couplings. In the embodiment shown, sleeves 508, 510 are similar to the previously described sleeves 208, 210. As with sleeves 208, 210, the sleeves 508, 510 contain a fluid 216 that has a viscosity which can be rapidly modified in response to an applied stimulus. But sleeves 508, 510 are somewhat different from sleeves 208, 210 insofar as they do not include exciter elements. Instead, one or more fluid couplings 506a, 506b are provided for each sleeve to provide a means for fluid to flow to/from the internal cavity defined by each fluid sleeve 508, 510 and a fluid reservoir 526. A pair of control elements 520a, 520b are provided along the length of fluid couplings 506a, 506b.

The control elements 520a, 520b each function in a manner similar to a valve to selectively vary the extent to which a flow of fluid 216 to and from the reservoir and each of the sleeves 508, 510 is facilitated or restricted. The control elements function by controlling a viscosity of the fluid 216 contained therein. For example, when a flow of the fluid in fluid couplings 506a, 506b is to be restricted, the viscosity of fluid contained in the control elements is increased. Conversely, when the flow of fluid is to be permitted, the viscosity of the fluid within the control elements is increased. The viscosity of the fluid contained in the control elements is varied by means of exciter elements $522_1$, $522_2$, $524_1$, $524_2$.

The exciter elements are arranged to apply a suitable stimulus to the fluid 216 in a manner similar to that which was described above. For example, is fluid 216 is an ER type fluid, then the exciter elements can be conductive plates. A voltage potential can then be applied by an activation voltage supply to set up an electric field between opposing ones of the plates. The voltage potential can be varied to control a viscosity of the fluid contained within the control elements 520a, 520b. Conversely, the exciter elements can be electromagnets which are used to selectively control a magnetic field applied to a MR type of fluid. In either scenario, the activation of the exciter elements selectively restricts the ability of the fluid to flow between the sleeves 508, 510 and the reservoir.

Compression of the flexible fluid containment layer 218 forming sleeves 508, 510 causes fluid to flow out of the fluid filled sleeves and into the reservoir 526. In some embodiments, it can be desirable to maintain the fluid in the reservoir at a somewhat elevated pressure so that when the compression force applied to a sleeve is removed, the fluid in the reservoir will tend to flow back into the sleeve from the reservoir. The elevated pressure can be maintained by means of a suitable compressor or pump (not shown).

In operation, the control elements will initially allow fluid to flow under slightly elevated pressure to the fluid chambers defined by the sleeves. If a force is applied to the exoskeleton, then the exoskeleton will exert a compression force upon one or more sleeves. This compression force will cause fluid to flow to the reservoir from each sleeve. Under these conditions, the sleeves will provide a soft resilient interface. However, if a more rigid interface is desired, the control elements will be caused to limit the flow of fluid between the sleeves and the reservoir. This will prevent fluid from exiting each sleeve and will provide an interface that is more stiff or rigid. Accordingly, the apparent stiffness of the viscous coupling formed by each sleeve 508, 510 is varied by selectively restricting the ability of the fluid to flow between the sleeves and the reservoir. In the embodiment shown in FIG. 5, two fluid couplings 506a, 506b are shown for each sleeve. Likewise, two control elements are 520a, 520b are provided (i.e., one for each fluid coupling). However, it should be understood that the invention is not limited in this regard and a greater or lesser number of fluid couplings and/or control elements can be used. Also, in some embodiments, it may be desirable to use an independent fluid coupling and control element for each sleeve 508, 510. Finally, it should be noted that the invention is not limited to use with toroidal shaped sleeves as shown. Instead, pads which extend only partially around a part of a human anatomy can be used in place of the sleeves.

Figure 6:
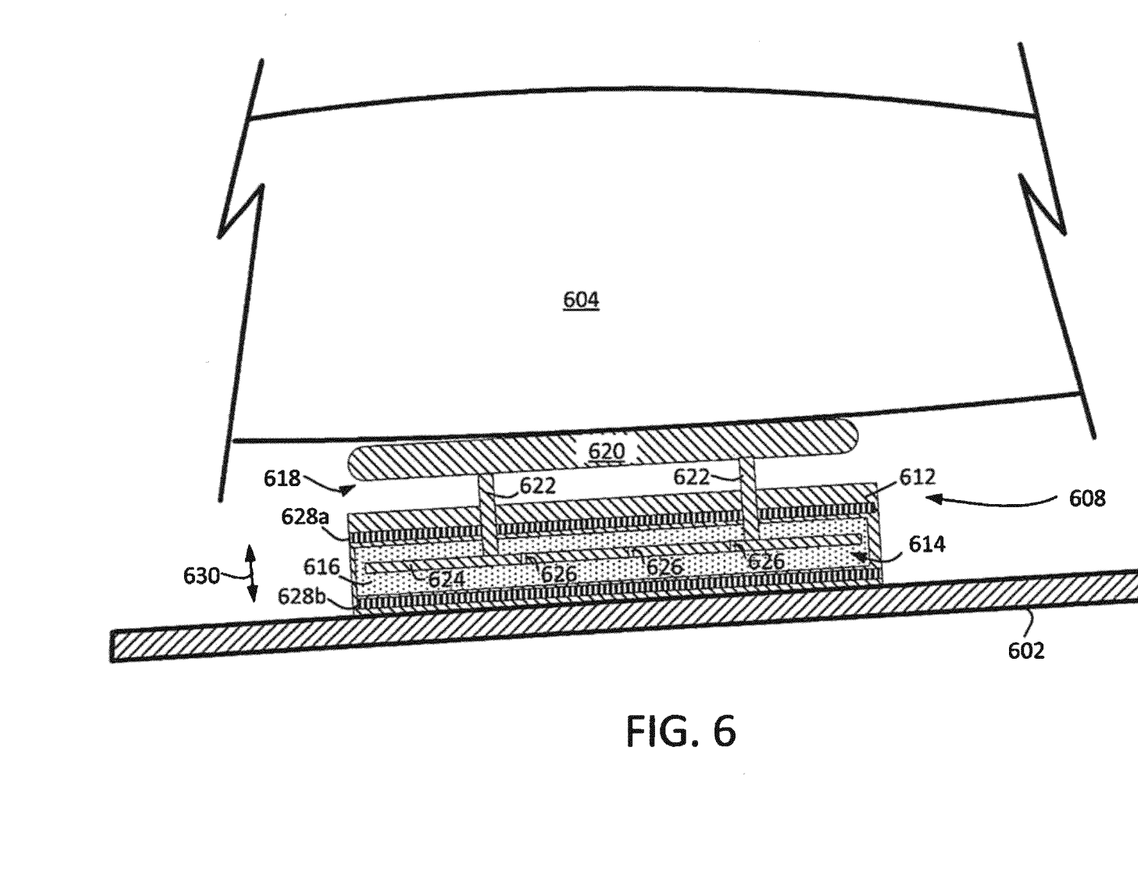
FIG. 6 is cross-sectional view of a portion of an exoskeleton that is useful for understanding a second alternative embodiment of the invention.

Note that other embodiments of viscous couplings are possible besides the arrangements of pads/sleeves described above. For example, in certain embodiments, the coupling between the operator and the exoskeleton could be through an interface mechanism that is conceptually similar to a cylindrical damper. The controllable fluid would be inside the damper, and by controlling the viscosity of the fluid the same behavior/result is achieved. For example, such an arrangement is shown in FIG. 6 which shows how a rigid portion of an exoskeleton 602 can be interfaced to a human operator 604 through a viscous coupling 608. The viscous coupling is comprised of a cylinder 612 which defines an internal cavity 614. A viscous fluid 616 is disposed within the internal cavity. The viscous fluid is of a type in which the viscosity can be selectively varied in accordance with an applied stimulus. For example, the viscous fluid can be an ER or MR fluid as described above. A plunger 618 is comprised of an interface plate 620 and one or more piston rods 622.

The piston rods extend into the internal cavity 614 and are connected to a piston head 624 which is movable in a direction indicated by arrow 630. The piston head optionally includes one or more orifices 626. One or more exciter elements 628a, 628b are provided for purposes of applying a stimulus to the viscous fluid 616. Depending on the type of fluid which is used, the exciter elements can be conductive metal plates or electro-magnets which establish an electric or magnetic field in the internal cavity 614. Accordingly, the viscosity of the fluid 616 can be selectively varied to control a stiffness of the interface between a human operator 604 and a rigid portion of the exoskeleton 602. The stimulus voltage or current applied to the exciter elements can be controlled in a manner similar to that which is described in relation to FIG. 4 to vary the viscosity of fluid 616. The piston head 624 movably interacts with the fluid 616 and experiences a variable resistance as the fluid is made more or less viscous by application of the stimulus.

Although only one viscous coupling 608 is shown in FIG. 6, it should be understood that the invention is not limited in this regard. A plurality of such viscous couplings can be provided at different locations within the exoskeleton to interact with different portions of an operator's anatomy. All such viscous couplings can be controlled by a control system similar to control system 224.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

We claim:

1. An exoskeleton system, comprising:
   an exoskeleton comprised of a plurality of structural members, one or more robotic joints at which the plurality of structural members are movably attached, and a plurality of actuators connected to the structural members which are capable of providing a motive force for moving the structural members in relation to the robotic joints, the structural members and robotic joints arranged to facilitate movement of the exoskeleton in conformance with at least a portion of a human anatomy when the exoskeleton is worn by a user;

a control system responsive to at least one input signal to generate actuator control signals which control the plurality of actuators;

wherein the exoskeleton includes at least one viscous coupling disposed at an interface location of said exoskeleton where a physical interaction occurs between a portion of the user and a portion of the exoskeleton when the exoskeleton is in use, the viscous coupling comprising a fluid having a viscosity selectively variable responsive to viscosity control signals from the control system.

2. The exoskeleton system according to claim 1, wherein said fluid is selected from the group consisting of an electrorheological (ER) fluid and magnetorehological (MR) fluid.

3. The exoskeleton system according to claim 1, further comprising at least one sensor communicatively coupled to the control system, and wherein the at least one input signal is provided by the at least one sensor.

4. The exoskeleton system according to claim 3, wherein the at least one sensor is selected from the group consisting of a force sensor, an acceleration sensor and a displacement sensor.

5. The exoskeleton system according to claim 4, wherein the control system is responsive to the input signal to automatically cause a reduction in said viscosity when a signal from the at least one sensor indicates the occurrence of at least one of a force, acceleration or displacement which exceeds a predetermined magnitude.

6. The exoskeleton system according to claim 4, wherein the control system comprises at least one predictive process which predicts an anticipated application of force to be experienced by the exoskeleton at a subsequent time, and wherein the control system automatically causes the viscosity to be reduced when the anticipated application of force is predicted to exceed a predetermined magnitude.

7. The exoskeleton system according to claim 1, wherein the viscous coupling is comprised of a pad or sleeve.

8. The exoskeleton system according to claim 1, wherein the viscous coupling is comprised of a flexible outer membrane which contains the fluid.

9. The exoskeleton system according to claim 1, wherein the viscous coupling is comprised of a fluid chamber in which the fluid is contained, a damping head disposed in and movably interacting with the fluid, and a connecting rod connected to the damping head.

10. A method for preventing discomfort to a user of a robotic exoskeleton, comprising:

determining the existence of an exoskeleton operating condition which has the potential to cause at least one of a discomfort or an injury to a user when the exoskeleton is being worn by the user;

responsive to the determining, selectively controlling with an exoskeleton control system at least one viscous coupling disposed at an interface location of said exoskeleton where a physical interaction occurs between a portion of the user and a portion of the exoskeleton when the exoskeleton is in use, wherein the controlling comprises selectively varying a viscosity of a fluid comprising the viscous coupling.

11. The method according to claim 10, wherein said fluid is selected from the group consisting of an electrorheological (ER) fluid and magnetorehological (MR) fluid.

12. The method according to claim 10, further comprising communicating the at least one input signal to the control system from at least one sensor disposed on said exoskeleton.

13. The method according to claim 12, further comprising sensing with the at least one sensor at least one of a force, an acceleration and a displacement experienced by at least a portion of the exoskeleton.

14. The method according to claim 13, further comprising automatically causing a reduction in said viscosity when the at least one sensor indicates at least one of a force, acceleration or displacement exceeds a predetermined magnitude.

15. The method according to claim 10, further comprising:

performing with the exoskeleton control system at least one predictive process to determine an anticipated application of force to be experienced by the exoskeleton at a subsequent time, and responsive to the performing step, automatically modifying said viscosity when the anticipated application of force to the exoskeleton is predicted to exceed a predetermined magnitude.

16. The method according to claim 10, further comprising containing the fluid in a pad or sleeve comprised of a flexible outer membrane.

17. The method according to claim 10, containing the fluid in a rigid fluid chamber, and interacting with the fluid using a movable connecting rod which is connected to a damping head disposed in the fluid.

18. The method according to claim 10, wherein said controlling step further comprises varying at least one of an electric field and a magnetic field to vary the viscosity of the fluid.

* * * * *